United States Patent
Philipp (10) Patent No.: US 8,271,092 B2
(45) Date of Patent: Sep. 18, 2012

(54) SWALLOWING STIMULATION SYSTEM

(75) Inventor: Jens Philipp, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 91 days.

(21) Appl. No.: 12/954,517

(22) Filed: Nov. 24, 2010

(65) Prior Publication Data

US 2011/0130808 A1 Jun. 2, 2011

Related U.S. Application Data

(60) Provisional application No. 61/264,854, filed on Nov. 30, 2009.

(51) Int. Cl.
*A61N 1/00* (2006.01)
(52) U.S. Cl. ........................................................ 607/59
(58) Field of Classification Search ............... 607/59, 607/47, 48, 148
See application file for complete search history.

(56) References Cited

U.S. PATENT DOCUMENTS

| 2006/0282010 A1 | 12/2006 | Martin |
| 2009/0048645 A1 | 2/2009 | Philipp |
| 2009/0284486 A1 | 11/2009 | Albus |
| 2010/0241191 A1* | 9/2010 | Testerman et al. .............. 607/48 |

FOREIGN PATENT DOCUMENTS

WO WO 2006/102626 9/2006

OTHER PUBLICATIONS

European Search Report dated Sep. 27, 2011. (6 pages).

* cited by examiner

*Primary Examiner* — George Manuel
*Assistant Examiner* — Robert N Wieland
(74) *Attorney, Agent, or Firm* — ARC IP Law, PC; Joseph J. Mayo (57) ABSTRACT

A swallowing stimulation system has a swallowing stimulator for use in triggering an act of swallowing in a patient. The swallowing system has an operating unit including operating elements for receiving user inputs, whereby the operating elements are allocated to different possible physical properties of a food, such that a user can allocate a particular food by means of the operating elements to at least one of at least two categories. The operating unit is designed to generate a control signal corresponding to a user input for the swallowing stimulator, and the swallowing stimulator is designed so that a stimulus for triggering an act of swallowing is formed in response to the control signal.

8 Claims, 9 Drawing Sheets

SWALLOWING STIMULATION SYSTEM

RELATED APPLICATION

This patent application claims the benefit of U.S. Provisional Patent Application No. 61/264,854, filed on Nov. 30, 2009, which is hereby incorporated by reference in its entirety.

TECHNICAL FIELD

The invention relates to the field of neuro-muscular stimulation, and in particular, to a swallowing stimulation system.

BACKGROUND

Swallowing stimulation systems are known in principle. They help patients who have swallowing disorders in which the triggering of the swallowing reflex is disturbed, but the swallowing reflex itself is usually preserved. In a healthy person, the shaping of the so-called food bolus at the end of the chewing process triggers the swallowing reflex by pressure of the masticated food exerted by the tongue against the palate. In a swallowing stimulation system, a sensor unit may be provided to recognize the formation of the food bolus by the tongue and then send an output signal to a swallowing stimulator which triggers the patient's swallowing reflex through a corresponding stimulus.

One difficulty that arises in practice is that the properties of the respective foods and accordingly the preparation of the foods in the mouth before swallowing differ greatly. For example, in a healthy person, a liquid such as a beverage flows quickly down the throat without any chewing action and the swallowing reflex is triggered. A piece of bread, however, is masticated in the mouth, softened and already predigested by a chewing action before the act of swallowing is triggered. Zwieback differs from a fresh piece of brown bread by its dry, mealy, crumbly consistency. This results in a different act of chewing and, in a healthy person, also a different act of swallowing. Thus, what is needed is a swallowing stimulation system that will take into account the variety of foods or beverages ingested.

SUMMARY

A swallowing stimulation system includes a patient device in the form of an operating unit, having operating elements to receive user input, such that the operating elements are assigned to different possible physical properties or consistencies of a food, so that a user can assign a particular food to at least one of at least two categories, according to its consistency. The operating unit is used to generate a control signal corresponding to user input for a swallowing stimulator. The swallowing stimulator forms a stimulus for triggering the act of swallowing in response to the control signal. The swallowing stimulator may also be connected to a sensor unit designed to detect the formation of a food bolus by a patient's tongue and to send a corresponding output signal to the swallowing stimulator, such that the swallowing stimulator then forms a corresponding stimulus for triggering the act of swallowing.

In the swallowing stimulator system, different parameter sets are preferably provided, optimally tailored to different foods, the particular preparation required in the patient's mouth and the triggering of the swallowing act and its optimization. The parameter sets preferably define different stimulation programs. Various parameter sets or stimulation programs need not be selected explicitly by the patient. The swallowing stimulator is instead designed to select a suitable parameter set or a suitable stimulation program as a function of the control signal generated by the operating unit.

By using the operating elements, the patient need only make entries about the consistency of the particular foods ingested, and in this way the patient can easily select a particular stimulation program suitable for different foods via the operating unit and transmit this to the stimulator. Different stimulation programs are defined by parameter sets, and each parameter set is assigned to one operating element.

A preferred swallowing stimulation system is one in which various parameter sets are stored in the operating unit, assigned to the operating elements, and in which the operating unit is designed to transmit a respective parameter set to the swallowing stimulator or the sensor unit or both after operation of an operating element by a user. Alternatively, the parameter sets may also be stored in the swallowing stimulator, and the operating unit may be designed to transmit only one control signal characterizing the user input to the swallowing stimulator, which then retrieves a control set stored in the swallowing stimulator.

The operating unit preferably has a graphic display and is designed to display icons symbolizing a physical property of foods on the display screen. The display is preferably a touch screen. A section of the touch screen assigned to an icon shown on the display then forms a particular operating element, which is activated by touching the display screen in the corresponding section. It is advantageous if the operating unit is designed to interpret double-clicking on a section of the display that forms a particular operating element as activation of this operating element in order to avoid inadvertent operation.

The present disclosure is also directed to a method for operating a swallowing stimulation system having a swallowing stimulator, which is designed for triggering an act of swallowing in a patient, whereby, the swallowing system has an operating unit with operating elements for receiving user inputs, whereby the operating elements are assigned to different possible physical properties of a food, such that a user can assign the particular food by means of the operating elements to at least one of at least two categories according to its consistency, the operating unit is designed to generate a control signal for the swallowing stimulator corresponding to the user input, and the swallowing stimulator is designed so that a stimulus for triggering an act of swallowing is triggered or formed as a function of the control signal.

DESCRIPTION OF THE DRAWINGS

The present invention will now be explained in greater detail on the basis of exemplary embodiments with reference to the figures. In the figures.

DETAILED DESCRIPTION

Figure 1:
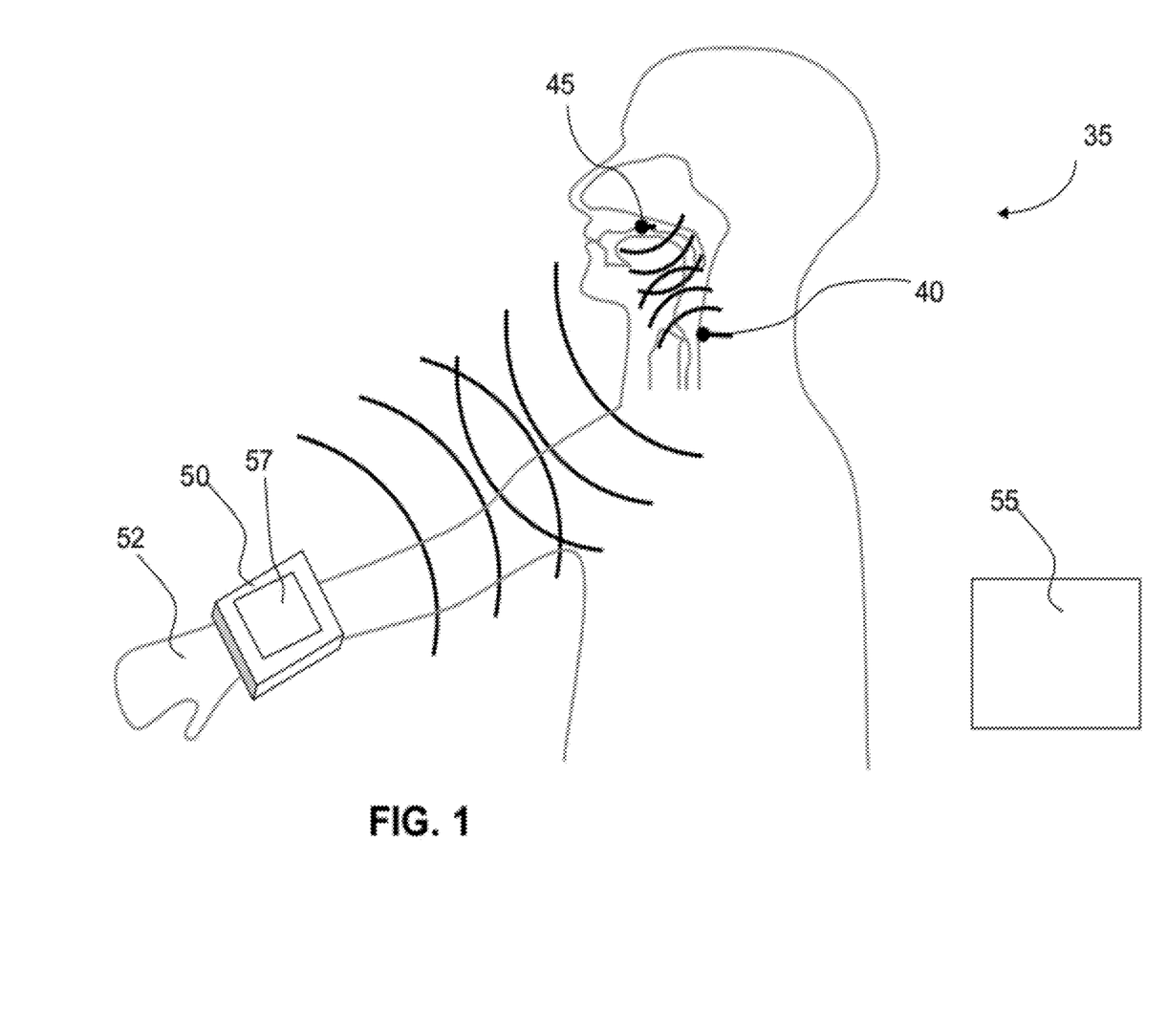
FIG. 1 shows a swallowing stimulation system having a swallowing stimulator and a patient device attached to the patient's wrist.
Figure 2:
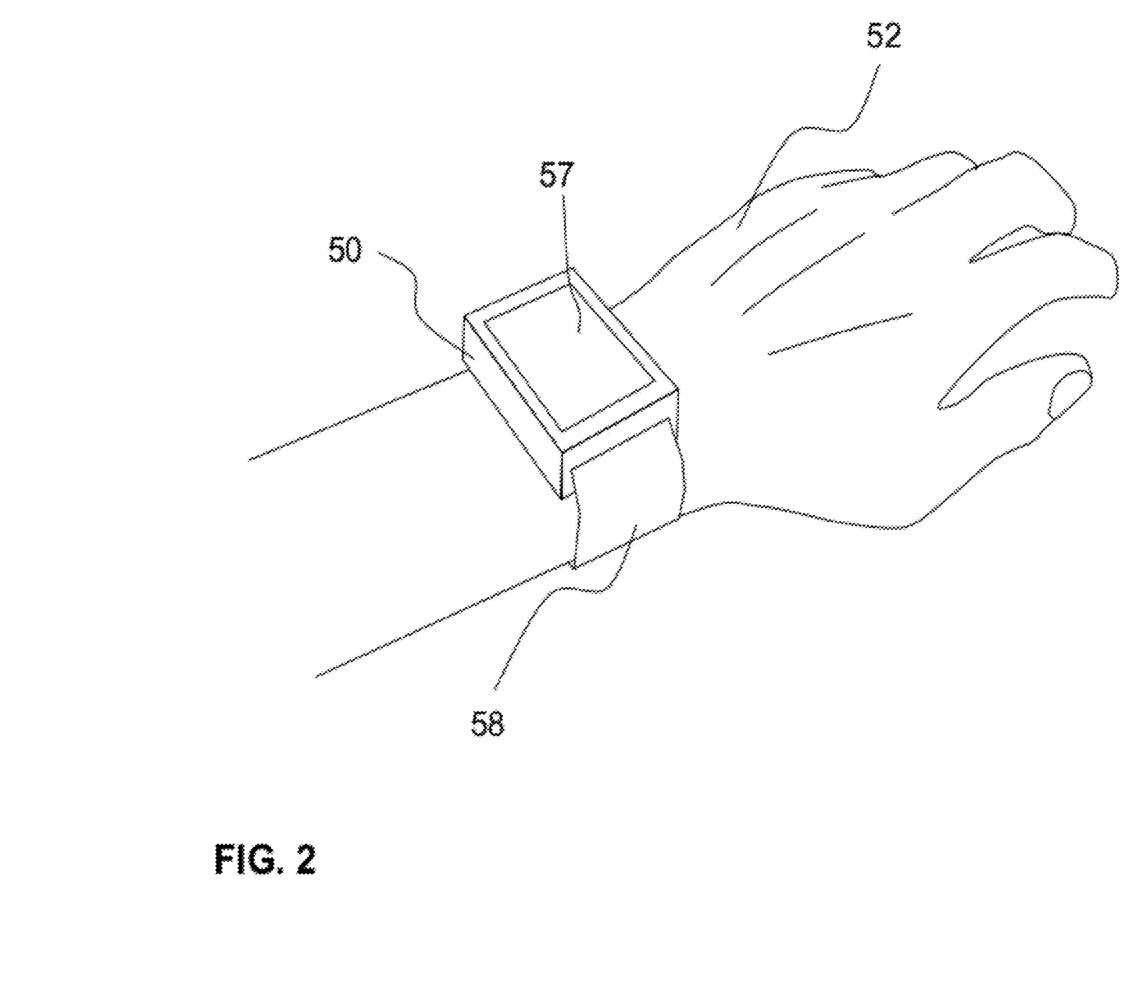
FIG. 2 shows a patient device for a swallowing stimulator.

With reference to FIGS. 1 and 2, FIG. 1 shows a swallowing stimulation system 35 having an implantable swallowing stimulator 40, an implantable sensor unit 45, which is wirelessly connected to the swallowing stimulator 40 and to an operating unit 50, which may be worn as a patient device on a patient's wrist 52. The operating unit 50 is able to communicate not only with the swallowing stimulator 40 but also with a remote service center 55 by way of a radio connection (e.g., mobile telephone). The sensor unit 45 serves as a triggering unit for the swallowing stimulator 40, both of which may be accommodated jointly in one device and may receive or provide their information via suitably positioned electrodes. Sensor unit 45 and stimulator 40 may also be embodied as two separate units communicating wirelessly, or via hard-wired electrodes, as suggested in FIG. 1. The operating unit 50 for the swallowing stimulation system 35, as shown in FIG. 2, contains a communication unit for the stimulator system 35 and a communication unit for communicating with the remote service center 55. The operating unit 50 has a display screen 57, preferably touch-sensitive, which at the same time represents the operating elements of the operating unit. Furthermore, the operating unit 50 may be provided with a wristband 58 so that operating unit 50, may be worn on the patient's wrist 52 in the manner of a wristwatch.

Different stimulation parameters may be used, depending on the foods to be ingested. Stimulation parameters for the swallowing stimulator 40, for use in recognizing when the chewing procedure is concluded may include, for example:

a threshold value to detect the pressure of the tongue against the palate, the number of pressure cycles until triggering of the swallowing reflex should occur, morphological properties of the pressure against the palate, e.g., steepness of the rise and drop in pressure, duration of the maximum pressure, and time between chewing motions.

delay time between detection of formation of the food bolus and delivery of the stimulation pulse, the stimulation pulse amplitude, the stimulation pulse length, number of pulses to be delivered, Type of pulse: current-controlled or voltage-controlled, Type of behavior if a stimulation pulse was not successful (non-capture):

renewed delivery of a (stronger) stimulation pulse, no renewed delivery of a stimulation pulse.

Parameter sets for particular sensing and stimulation patterns may be stored in one or more system components, namely operating unit 50, sensor unit 45 and implantable swallowing stimulator 40.

Figure 3:
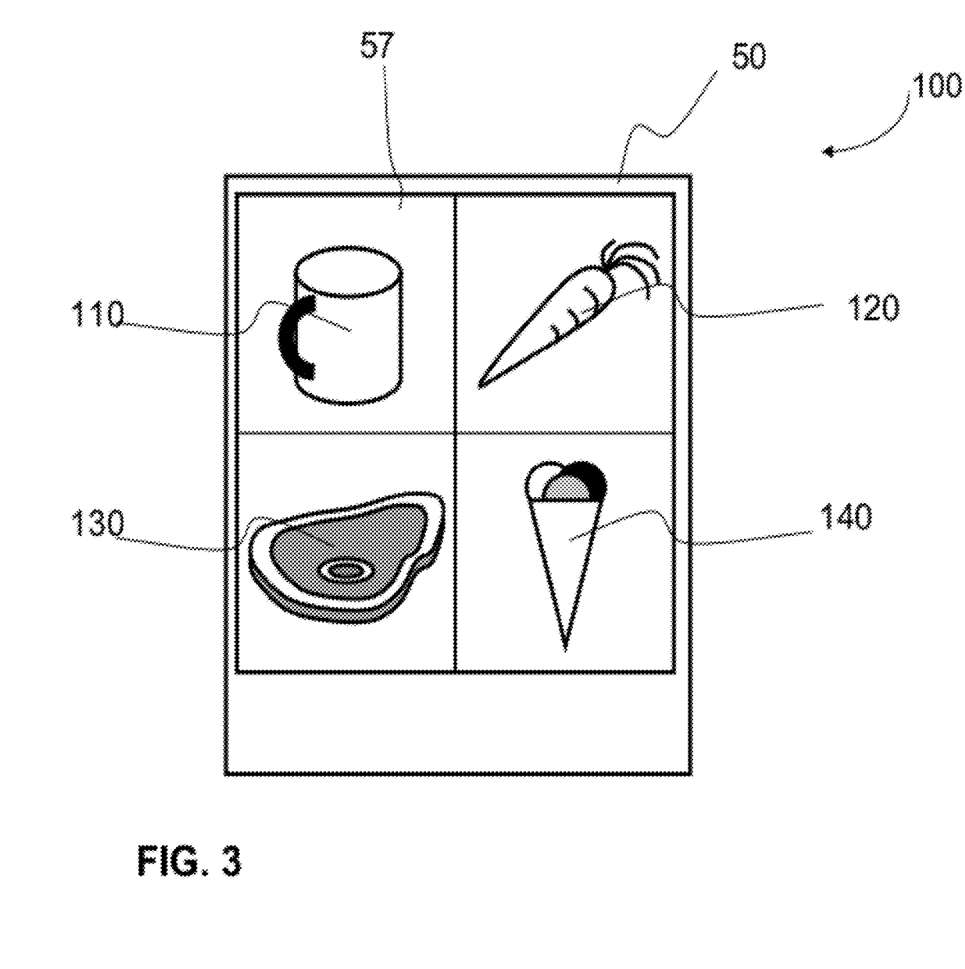
FIG. 3 shows an example of a first variant of a user interface of the patient device.

In a first variant of operating unit 50 shown in FIG. 3, a number of different operating elements are displayed on the touch display screen 57, represented here by four exemplary icons 110-140. Each icon symbolizes a certain food or its most important physical properties, with regard to chewing and swallowing, that preferably may be selected by touching the icon. For example, a first icon 110 symbolizes a beverage; a second icon 120 symbolizes a raw vegetable such as a carrot; a third icon 130 symbolizes meat, for example, a steak; and a fourth icon 140 symbolizes a soft food like ice cream. Coupled with each icon is a suitable parameter set for the swallowing stimulator 40, which is either stored in the operating unit 50, where it is assigned to a particular icon and is transmitted to the swallowing stimulator 40 when selected, or a command that is transmitted to the swallowing stimulator 40 and selects the respective parameter set stored in the stimulator 40. The advantage of this variant is that it is simple to implement, and the display screen 57 needs only one key field per parameter set or icon, i.e., four fields are needed for the example shown in FIG. 3.

To avoid inadvertent misadjustment of a particular selected program, suitable mechanisms, e.g., double-clicking, may be provided, i.e., the operating unit 50 may be designed to detect double-clicking on a corresponding icon and to interpret that as user input. Likewise, the control signals assigned to a user input are transmitted to the swallowing stimulator 40 using known security mechanisms, e.g., checksums.

Figure 4A:
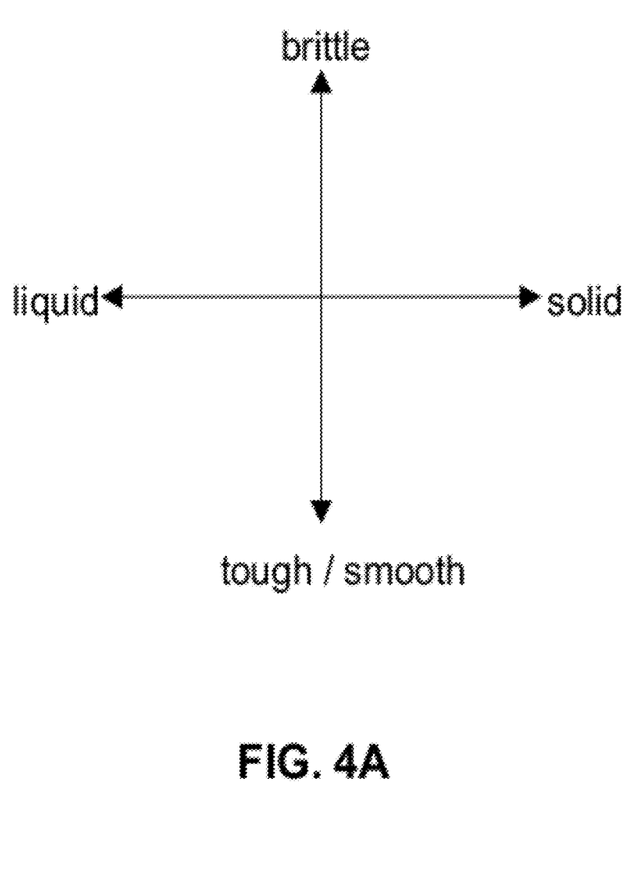
FIG. 4a shows pairs of properties describing the physical nature of food spanning a coordinate plane.
Figure 4B:
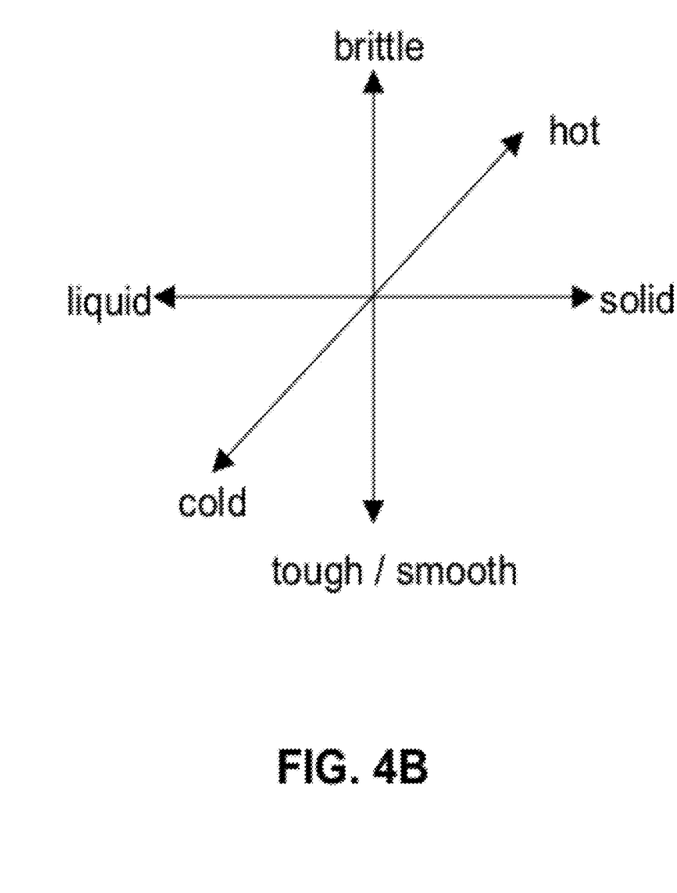
FIG. 4b shows pairs of properties describing the physical nature of food as spanning a coordinate space.

FIG. 4 shows an example of different physical properties of foods. If two pairs of food properties are plotted on orthogonal axes, it is possible to span a coordinate plane, and if three pairs of food properties are plotted on orthogonal axes it is possible to span a volumetric space. Two pairs may be displayed directly on the plane of the touch display screen 57. Three or more pairs may be implemented by suitable interfacing, e.g., through multiple displays, additional buttons, slide bar controls, and the like. As the examples used here, SOLID and LIQUID may be mentioned here as a pair of food properties as well as BRITTLE and TOUGH/SMOOTH. Other pairs may include HOT and COLD. Other pairs of properties are also conceivable.

Figure 5:
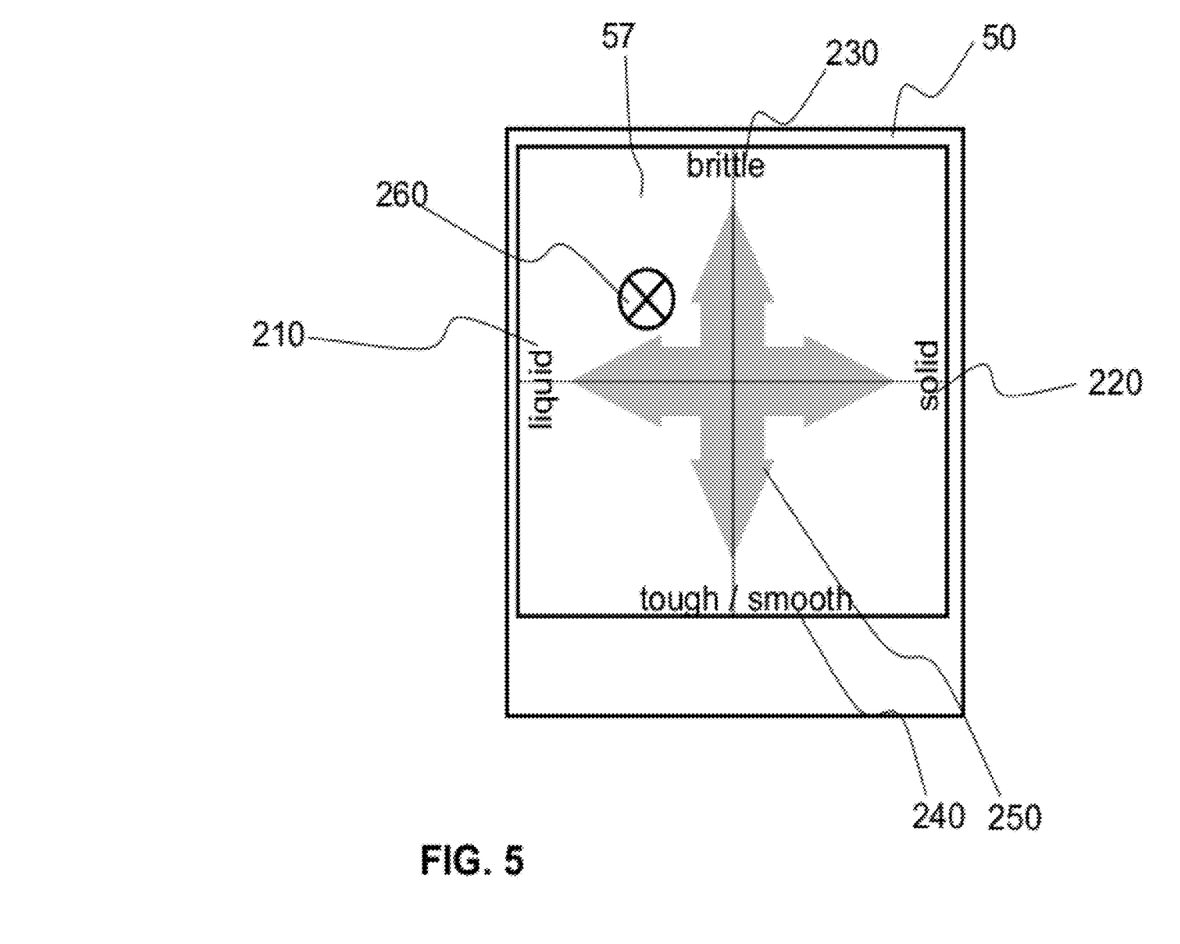
FIG. 5 shows an example of a second variant of a user interface of the patient device.

FIG. 5 shows two of these pairs of food properties: a first pair 210/220, and a second pair 230/240, arranged in a two-dimensional coordinate space, on the touch display screen 57 of the operating unit 50. Bi-directional arrows 250 indicate an operating element in the form of a continuum along each orthogonal axis of the coordinate space, which is spanned in a two-dimensional form. Combinations of properties may be selected by a cursor 260.

Figure 6:
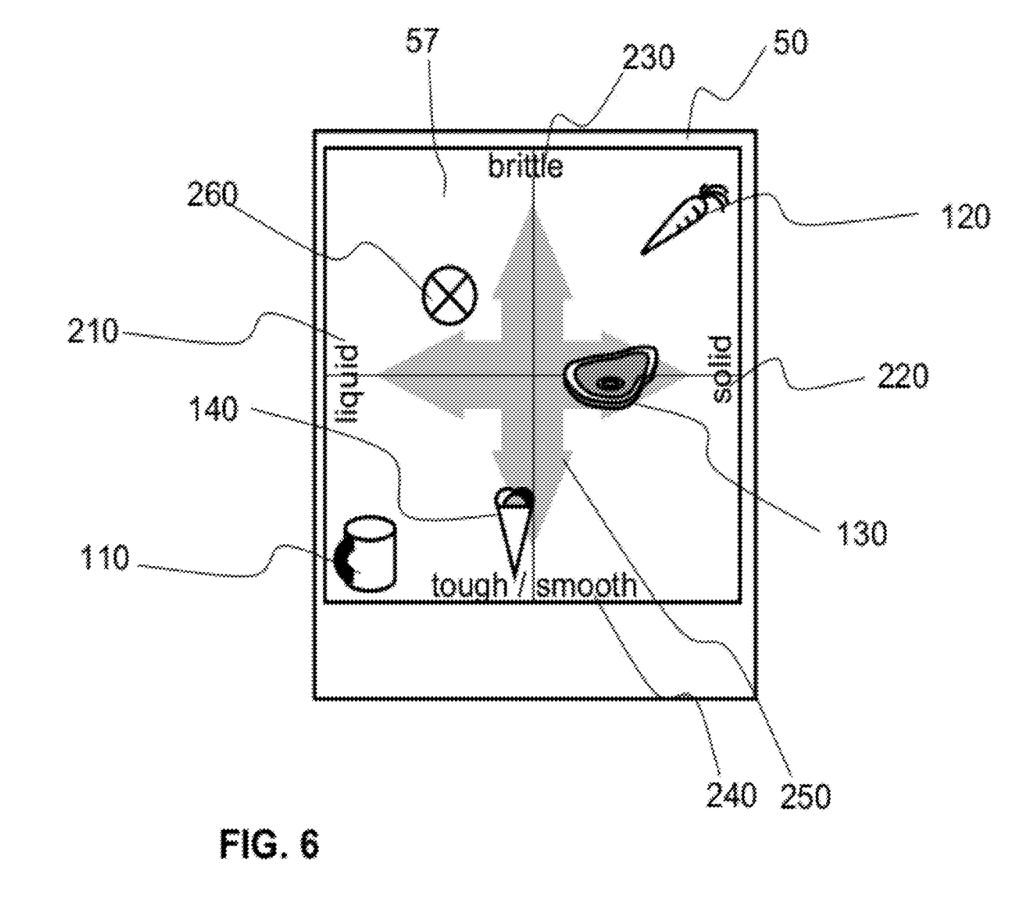
FIG. 6 shows an example of a third variant of a user interface of the patient device.

To further simplify user selection, certain icons representing foods may be placed directly on the coordinate plane according to their fundamental properties, as shown in FIG. 6. An advantage in comparison with the method of selection shown in FIG. 3 is that the food properties on which the icons are based are immediately discernible and serve as landmarks to orient the user, as an improvement over the display shown in FIG. 5. Another advantage is that the user can immediately perform fine adjustments of the stimulation program. For example, the user may optimize the consumption of a vegetable soup by pressing not on the mug but instead at a point slightly more toward the center, to indicate a more solid, more brittle substance, depending on the ingredients of the soup.

The swallowing stimulation system 35 disclosed herein thus offers a simple choice between suitable parameter sets which are optimally coordinated for different foods, the required preparation in the patient's mouth, and the triggering of the act of swallowing and its optimization.

The patient may simply select a particular program suitable for different foods by way of the operating unit as an external device, and by transmitting this to the swallowing stimulator 40. This allows a selection of stored parameter sets also in addition to "ad hoc" adjustments.

Figure 7:
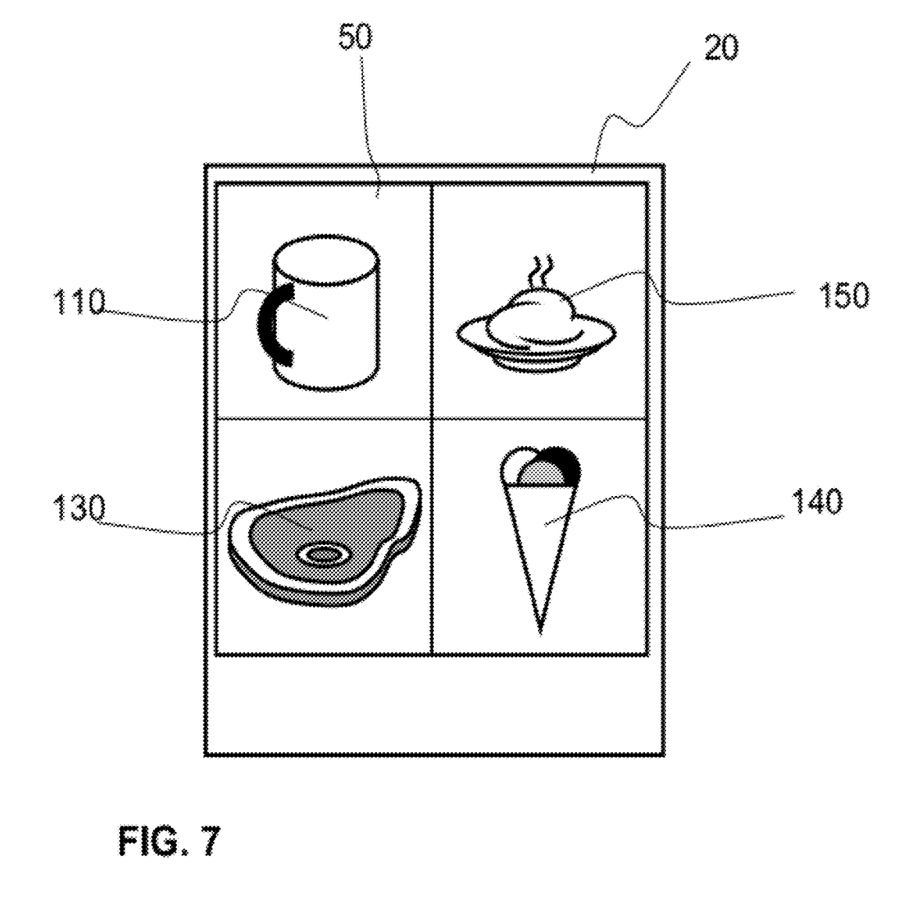
FIG. 7 shows an example of a fourth variant of a user interface of the patient device.

FIG. 7 shows a further variant of the user interface shown in FIG. 3. Icons shown in FIG. 7 represent physical properties of the food such as, for example, liquid 110, mashed 150, solid 130 and smooth 140. The variant shown in FIG. 7 will be used to describe exemplarily drinking and the swallowing of mashed food. The following table presents an overview of potentially relevant parameters and their range of values:

TABLE 1

Swallowing Stimulator Parameter Values
Parameter Set needed for the Swallowing Stimulator

| Preset Parameters | Preset Value | Dimension | Possible Values | Comment |
| --- | --- | --- | --- | --- |
| P_Min | 0.5-20 typical | [N/cm$^2$] | 0 . . . n | Minimal Pressure to start T_P_Min time window |
| Chew_Count_Min | 1-20 typical | — | 0 . . . n | Number of chews to detect before swallowing is triggered by stimulation pulse |
| T_P_Min | 50-1000 typical | [ms] | 0 . . . n | Minimal time where pressure must be above P_Min to count as a chew |
| T_Chew_Max | 1-20 typical | [ms] | 0 . . . n | Maximum time between to chews |
| T_Stim_Delay | 10-1000 typical | [ms] | 0 . . . n | Time between detection of Chew_Count_Min and stimulation pulse delivery |
| Pulse_Type | V or C | — | V, C | V = Voltage_Control, C = Current_Control |
| U_Stim | 0.5-20 typical | [V] | 0 . . . n | Voltage of Stimulation Pulse (when Pulse_Type = V) |
| I_Stim | 0.01-20 typical | [mA] | 0 . . . n | Current of Stimulation Pulse (when Pulse_Type = C) |
| T_Stim | 0.01-100 typical | [ms] | 0 . . . n | Length of stimulation pulse |
| Count_Stim | 1-20 typical | — | 0 . . . n | Number of stimulation pulses to be delivered as a train |
| T_Capture_Delay_Max | 1-500 typical | [ms] | | Maximum time after pulse delivery by which a capture must be detected. |
| U_Capture_Detect_Min | 0.01-20 typical | [mV] | | Min EMG voltage measured by electrode to start T_Capture_Detect time window |
| T_Capture_Detect_Min | 1-20 typical | [ms] | | Minimal time where U_EMG must be above U_Capture_Detect_Min to count as a successful stimulation |
| T_Capture_Delay | 0.1-200 typical | [ms] | | Time after pulse delivery, waiting for Capture_Detected = TRUE |
| Back_Up_Pulse | On/Off | — | On/Off | If first pulse was not successful, deliver another? |
| U_Stim_BU | 0.5-20 typical | [V] | 0 . . . n | Voltage of Back-Up Stimulation Pulse Pulse (when Pulse_Type = V AND Back_Up_Pulse = On) |
| I_Stim_BU | 0.01-20 typical | [mA] | 0 . . . n | Current of Back-Up Stimulation Pulse Pulse (when Pulse_Type = C AND Back_Up_Pulse = On) |
| Use_Morphology | On/Off | | On/Off | Use of P curve shape, e.g. speed of pressure rise/fall |
| Vel_P_Rise_Min | 0.1-200 | [N/cm$^2$s] | 0 . . . n | Minimum speed with which pressure rises (when Use_Morphology = On) |
| Vel_P_Fall_Min | 0.1-200 | [N/cm$^2$s] | 0 . . . n | Minimum speed with which pressure drops (when Use_Morphology = On) |

Table 2 gives an overview of measured values and the sources from which they are derived:

TABLE 2

Sources of swallowing stimulator parameter values

| Measured & Derived Parameters | Dimension | Possible Values | Comment |
|---|---|---|---|
| P | Measured | [N/cm$^2$] | | Pressure against palate |
| T_P | Measured | [s] | | Measured time with P > P_min |
| Vel_P_Rise | Measured | [N/cm$^2$s] | 0 . . . n | Speed with which pressure rises (when Use_Morphology = On) |
| Vel_P_Fall | Measured | [N/cm$^2$s] | 0 . . . n | Speed with which pressure drops (when Use_Morphology = On) |
| Chew_Detect | Derived from T_Chew_max, P_Min, T_P_Min | — | FALSE or TRUE | Chew has been detected |
| Chew_Count | Derived from P and T_P_Min | — | | Increased by 1 when P > P_Min for more than T_P_Min |
| T_Chew | Measured | [s] | 0 . . . n | Time between two increases of Chew_Count, must be < T_Chew_max to count the chews as one action |
| U_EMG | Measured | [mV] | | Electrical recording of muscle activity at electrode |
| Capture_Detected | Derived from U_EMG | — | FALSE or TRUE | Set when U_EMG > U_Capture_Detect_Min for more than T_Capture_Detect_Min |

Figure 8:
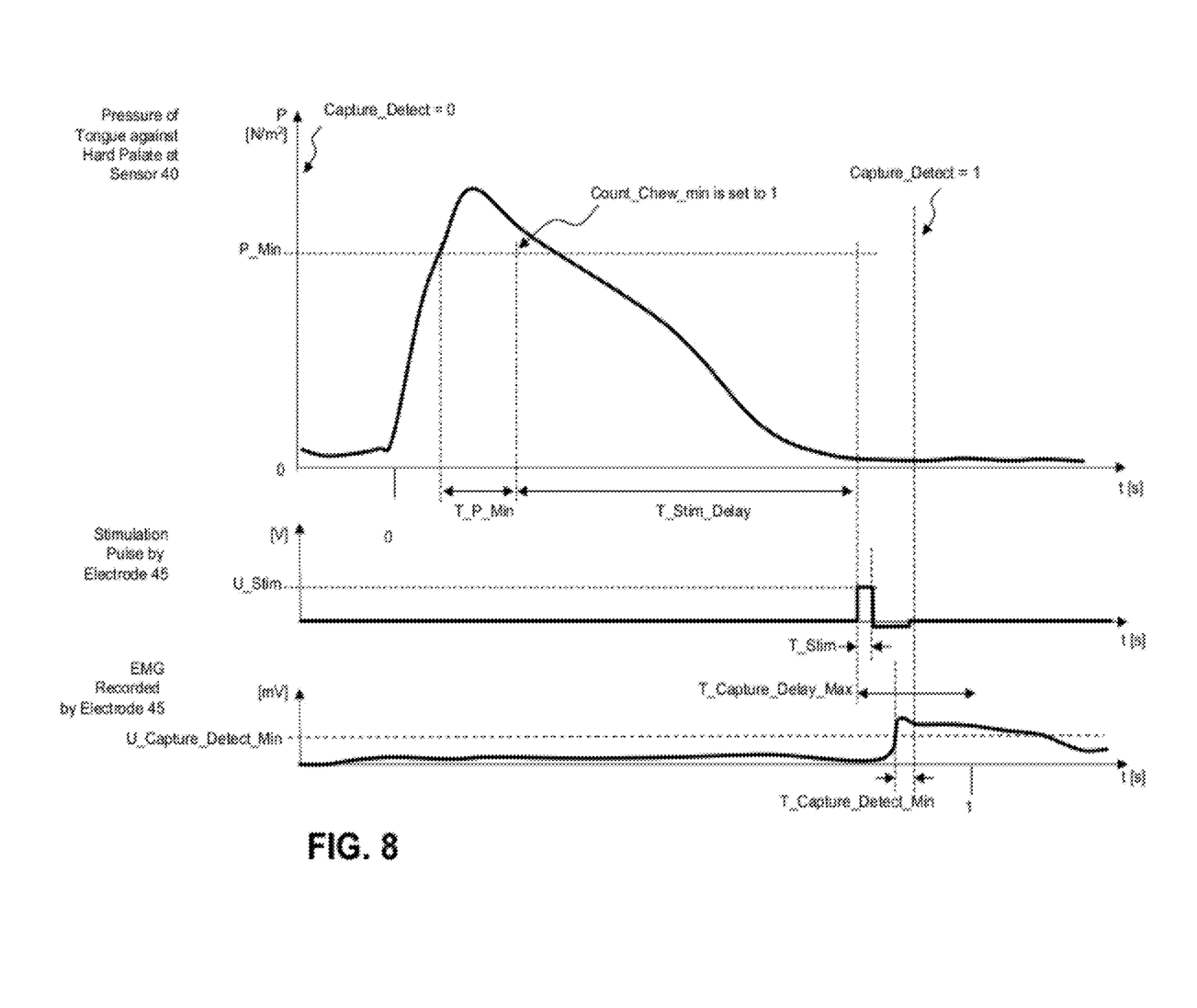
FIG. 8 shows diagrams with parameters for a mode for drinking.

FIG. 8 shows diagrams for stimulating drinking. It should be mentioned that it is assumed that the swallowing behaviour for "dry swallowing" and drinking are the same. Therefore the following parameter set should be adequate for "dry swallowing," clearance of saliva and drinking. Therefore the parameter P_Min, describing the minimum pressure of the tongue against sensor 45 to start the T_P_Min time window in which P_Min must be exceeded, shown in FIG. 8 on the upper ordinate is set to a value of about 2 N/cm$^2$. To trigger the swallowing the pressure P_Min has to exceed during the time window T_P_Min, which is true for FIG. 8. Due to the patient's choice of swallowing a liquid the Count_Chew_min parameter describing the minimum of chews before swallowing, is set to 1, while a chew is detected as described above by the pressure of the tongue to sensor 45 which exceeds P_Min for at least a time window T_P_Min. The stimulation of the swallowing process is delayed by the adjustable time T_Stim_Delay which is patient dependent and for example between 10 ms and 1000 ms, preferably about 0.6 s.

The following parameters are examples to allow the stimulation of a swallowing process of a liquid:

TABLE 3

Parameter values for an exemplary "Drink" program of a swallowing stimulator
Parameter Set for Mode DRINK (110)

| | Preset Value | Dimension | Possible Values | Comment |
|---|---|---|---|---|
| Preset Parameters | | | | |
| P_Min | 1.2 | [N/cm$^2$] | 0 . . . n | Minimal Pressure to start T_P_Min time window |
| Chew_Count_Min | 1 | — | 0 . . . n | Number of chews to detect before swallowing is triggered by stimulation pulse |
| T_P_Min | 0.2 | [s] | 0 . . . n | Minimal time where pressure must be above P_Min to count as a chew |
| T_Chew_Max | 2000 | [ms] | 0 . . . n | Maximum time between to chews |
| T_Stim_Delay | 0.6 | [s] | 0 . . . n | Time between detection of Chew_Count_Min and stimulation pulse delivery |
| Pulse_Type | V | — | V, C | V = Voltage_Control, C = Current_Control |

TABLE 3-continued

Parameter values for an exemplary "Drink" program of a swallowing stimulator
Parameter Set for Mode DRINK (110)

| | Preset Value | Dimension | Possible Values | Comment |
|---|---|---|---|---|
| U_Stim | 5 | [V] | 0 ... n | Voltage of Stimulation Pulse (when Pulse_Type = V) |
| I_Stim | Not applicable here, because Pulse_Type = V | [mA] | 0 ... n | Current of Stimulation Pulse (when Pulse_Type = C) |
| T_Stim | 5 | [ms] | 0 ... n | Length of stimulation pulse |
| Count_Stim | 1 | — | 0 ... n | Number of stimulation pulses to be delivered as a train |
| T_Capture_Delay_Max | 10 | [ms] | | Maximum time after pulse delivery by which a capture must be detected. |
| U_Capture_Detect_Min | 3 | [mV] | | Min EMG voltage measured by electrode to start T_Capture_Detect time window |
| T_Capture_Detect_Min | 10 | [ms] | | Minimal time where U_EMG must be above U_Capture_Detect_Min to count as a successful stimulation |
| T_Capture_Delay | 10 | [ms] | | Time after pulse delivery, waiting for Capture_Detected = TRUE |
| Back_Up_Pulse | On | — | On/Off | If first pulse was not successful, deliver another? |
| U_Stim_BU | 7 | [V] | 0 ... n | Voltage of Back-Up Stimulation Pulse Pulse (when Pulse_Type = V AND Back_Up_Pulse = On) |
| I_Stim_BU | Not applicable, because Pulse_Type = V | [mA] | 0 ... n | Current of Back-Up Stimulation Pulse Pulse (when Pulse_Type = C AND Back_Up_Pulse = On) |
| Use_Morphology | Off | On/Off | | Use of P curve shape, e.g. speed of pressure rise/fall |
| Vel_P_Rise_Min | Not needed because Use_Morphology = Off | [N/cm$^2$s] | 0 ... n | Minimum speed with which pressure rises (when Use_Morphology = On) |
| Vel_P_Fall_Min | Not needed because Use_Morphology = Off | [N/cm$^2$s] | 0 ... n | Minimum speed with which pressure drops (when Use_Morphology = On) |
| Measured & Derived Parameters | | | | |
| P | Measured | [N/cm$^2$] | | Pressure against palate |
| T_P | Measured | [s] | | Measured time with P > P_min |
| Vel_P_Rise | Not applicable, because Use_Morphology = Off | [N/cm$^2$s] | 0 ... n | Speed with which pressure rises (when Use_Morphology = On) |
| Vel_P_Fall | Not applicable, because Use_Morphology = Off | [N/cm$^2$s] | 0 ... n | Speed with which pressure drops (when Use_Morphology = On) |
| Chew_Detect | Derived from T_Chew_max, P_Min, T_P_Min | — | FALSE or TRUE | Chew has been detected |
| Chew_Count | Derived from P and T_P_Min | — | | Increased by 1 when P > P_Min for more than T_P_Min |
| T_Chew | Measured | [s] | 0 ... n | Time between two increases of Chew_Count, must be < T_Chew_max to count the chews as one action |

TABLE 3-continued

Parameter values for an exemplary "Drink" program of a swallowing stimulator
Parameter Set for Mode DRINK (110)

| | Preset Value | Dimension | Possible Values | Comment |
|---|---|---|---|---|
| U_EMG | Measured | [mV] | — | Electrical recording of muscle activity at electrode |
| Capture_Detected | Derived from U_EMG | — | FALSE or TRUE | Set when U_EMG > U_Capture_Detect_Min for more than T_Capture_Detect_Min |

If the user selects the program "Drink" by touching the corresponding beverage icon 110 on the touch display screen 57 of operating unit 50, the above parameter set for "Drink" 110 is loaded and the stimulation program is started:
The program waits to detect a chew by waiting for a minimum pressure P_Min to appear for at least the time T_P_Min at the site of the pressure sensor 45. When that happens Chew_Count is increases from 0 to 1.

A delay time T_Stim_Delay is given to allow the liquid to be moved into the throat. Then the stimulation pulse is delivered at the site of swallowing stimulator 40.

In this example the stimulation pulse is given to be successful, meaning that it stimulates the superior laryngeal nerve to activate the sphincter muscle. Activation of the sphincter muscle results in an increase of muscle activity which can be detected via electromyography recording EMG. The muscle activity is measured via the implantable sensor unit 45. If the measured Voltage U_EMG is above U_Capture_Detect_Min for at least the time T_Capture_Detect_Min, a Capture, i.e. successful stimulation of the muscle is detected. Here the swallowing stimulation program terminates. The same or another program for swallowing can be triggered by selecting a food type displayed on the touch display screen 57 of operating unit 50.

Figure 9:
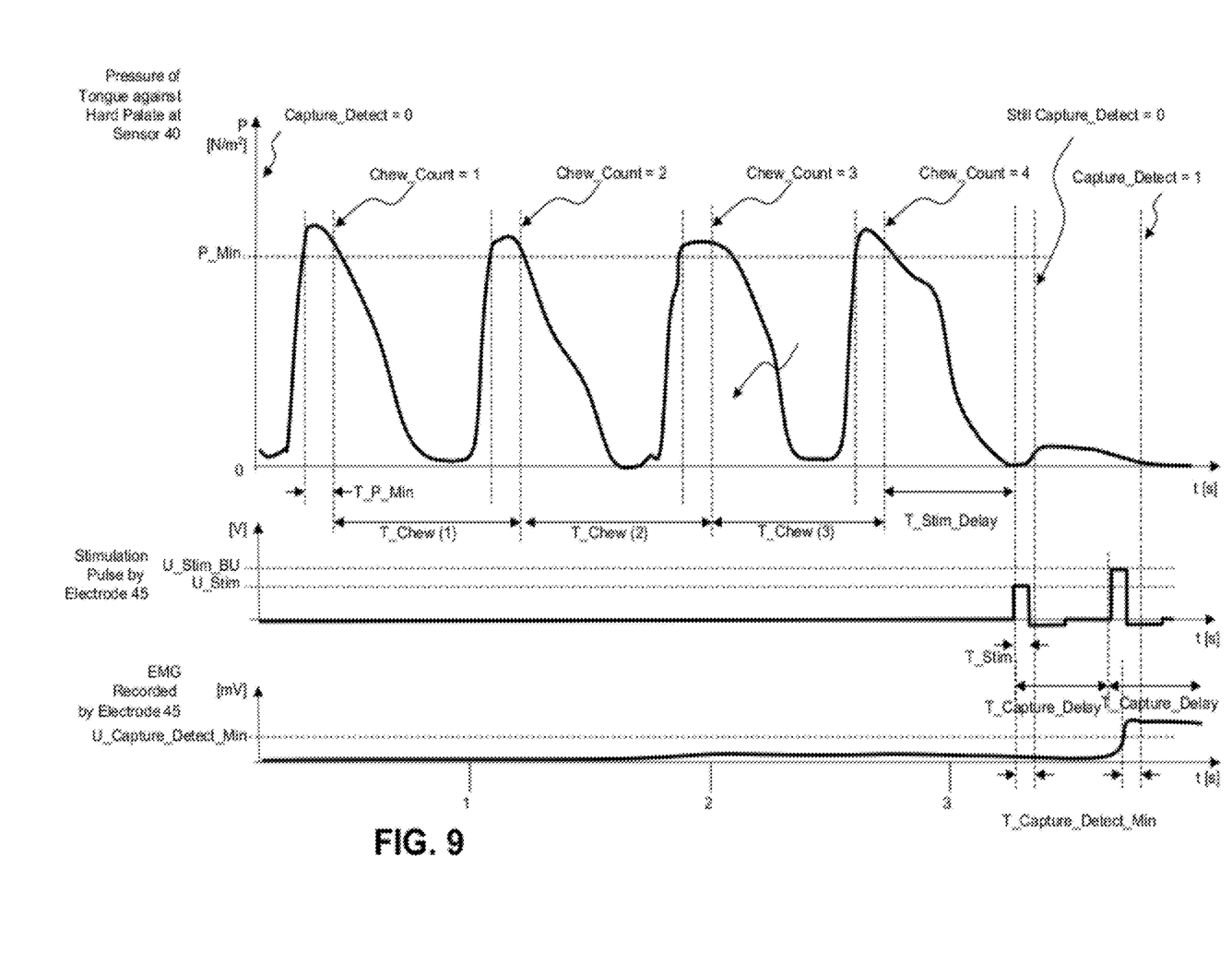
FIG. 9 shows diagrams with parameters for a mode for swallowing mashed food.

FIG. 9 shows a diagram for stimulating a swallowing process for mashed food. Therefore the parameter P_Min, describing the minimum pressure of the tongue against sensor unit 45 to start the T_P_Min time window in which P_Min must be exceeded, shown in FIG. 9 on the upper ordinate is set to a value of about 4 N/cm$^2$. To trigger the swallowing the pressure P_Min has to exceed during the time window T_P_Min, which is true for FIG. 9. Due to the patients choice of swallowing mashed food the Count_Chew_min parameter describing the minimum of chews before swallowing, is set to 4, while a chew is detected as described above by the pressure of the tongue to sensor unit 45 which exceeds P_Min for at least a time window T_P_Min. The stimulation of the swallowing process is delayed by the adjustable time T_Stim_Delay which is patient dependent and for example between 10 ms and 1000 ms, preferably about 0.6 s.

The following parameters are examples to allow the stimulation of a swallowing process of mashed food:

TABLE 4

Parameter values for an exemplary "Mashed Food" program of a swallowing stimulator
Parameter Set for Mode MASHED FOOD (150)

| | Preset Value | Dimension | Possible Values | Comment |
|---|---|---|---|---|
| Preset Parameters | | | | |
| P_Min | 4 | [N/cm$^2$] | 0 ... n | Minimal Pressure to start T_P_Min time window |
| Chew_Count_Min | 4 | — | 0 ... n | Number of chews to detect before swallowing is triggered by stimulation pulse |
| T_P_Min | 0.2 | [s] | 0 ... n | Minimal time where pressure must be above P_Min to count as a chew |
| T_Chew_Max | 2000 | [ms] | 0 ... n | Maximum time between to chews |
| T_Stim_Delay | 0.6 | [s] | 0 ... n | Time between detection of Chew_Count_Min and stimulation pulse delivery |
| Pulse_Type | V | — | V, C | V = Voltage_Control, C = Current_Control |
| U_Stim | 5 | [V] | 0 ... n | Voltage of Stimulation Pulse (when Pulse_Type = V) |
| I_Stim | Not applicable here, because Pulse_Type = V | [mA] | 0 ... n | Current of Stimulation Pulse (when Pulse_Type = C) |
| T_Stim | 5 | [ms] | 0 ... n | Length of stimulation pulse |
| Count_Stim | 1 | — | 0 ... n | Number of stimulation pulses to be delivered as a train |

TABLE 4-continued

Parameter values for an exemplary "Mashed Food" program of a swallowing stimulator
Parameter Set for Mode MASHED FOOD (150)

| | Preset Value | Dimension | Possible Values | Comment |
|---|---|---|---|---|
| T_Capture_Delay_Max | 10 | [ms] | | Maximum time after pulse delivery by which a capture must be detected. |
| U_Capture_Detect_Min | 3 | [mV] | | Min EMG voltage measured by electrode to start T_Capture_Detect time window |
| T_Capture_Detect_Min | 10 | [ms] | | Minimal time where U_EMG must be above U_Capture_Detect_Min to count as a successful stimulation |
| T_Capture_Delay | 10 | [ms] | | Time after pulse delivery, waiting for Capture_Detected = TRUE |
| Back_Up_Pulse | On | — | On/Off | If first pulse was not successful, deliver another? |
| U_Stim_BU | 7 | [V] | 0 . . . n | Voltage of Back-Up Stimulation Pulse Pulse (when Pulse_Type = V AND Back_Up_Pulse = On) |
| I_Stim_BU | Not applicable, because Pulse_Type = V | [mA] | 0 . . . n | Current of Back-Up Stimulation Pulse Pulse (when Pulse_Type = C AND Back_Up_Pulse = On) |
| Use_Morphology | Off | | On/Off | Use of P curve shape, e.g. speed of pressure rise/fall |
| Vel_P_Rise_Min | Not needed because Use_Morphology = Off | [N/cm$^2$s] | 0 . . . n | Minimum speed with which pressure rises (when Use_Morphology = On) |
| Vel_P_Fall_Min | Not needed because Use_Morphology = Off | [N/cm$^2$s] | 0 . . . n | Minimum speed with which pressure drops (when Use_Morphology = On) |
| Measured & Derived Parameters | | | | |
| P | Measured | [N/cm$^2$] | | Pressure against palate |
| T_P | Measured | [s] | | Measured time with P > P_min |
| Vel_P_Rise | Not applicable, because Use_Morphology = Off | [N/cm$^2$s] | 0 . . . n | Speed with which pressure rises (when Use_Morphology = On) |
| Vel_P_Fall | Not applicable, because Use_Morphology = Off | [N/cm$^2$s] | 0 . . . n | Speed with which pressure drops (when Use_Morphology = On) |
| Chew_Detect | Derived from T_Chew_max, P_Min, T_P_Min | — | FALSE or TRUE | Chew has been detected |
| Chew_Count | Derived from P and T_P_Min | — | | Increased by 1 when P > P_Min for more than T_P_Min |
| T_Chew | Measured | [s] | 0 . . . n | Time between two increases of Chew_Count, must be < T_Chew_max to count the chews as one action |
| U_EMG | Measured | [mV] | | Electrical recording of muscle activity at electrode |
| Capture_Detected | Derived from U_EMG | — | FALSE or TRUE | Set when U_EMG > U_Capture_Detect_Min for more than T_Capture_Detect_Min |

To show the functionality of the back-up pulse in the example, the first stimulation pulse shall not be successful, so that the back-up pulse is triggered. The user selects the program "Mashed Food" by selecting the representative fourth icon 140 on the touch display screen 57 of operating unit 50. The above parameter set for "Mashed Food" is loaded and the stimulation program is started:

The program waits to detect a chew by waiting for a minimum pressure P_Min to appear for at least the time T_P_Min at the site of the pressure sensor unit 45. When that happens Chew_Count increases from 0 to 1. The program then waits to detect further chews as described above until Chew_Count=Chew_Count Min, which, in this case, equals 4.

A delay time T_Stim_Delay is given to allow the food to be moved into the throat.

Then a stimulation pulse is delivered via swallowing stimulator 40.

In this example the stimulation pulse is given to be successful, meaning that it stimulates the superior laryngeal nerve to activate the sphincter muscle. Activation of the sphincter muscle results in an increase of muscle activity which can be detected via electromyography recording EMG. This is measured via the implantable sensor unit 45. If the measured Voltage U_EMG is above U_Capture_Detect_Min for at least the time T_Capture_Detect_Min, a Capture, i.e., a successful stimulation of the muscle is detected. This is not the case in this example. Therefore a back-up stimulation pulse utilizing a higher voltage U_Stim_Bu is delivered. Again, U_EMG is measured and this time it remains above U_Capture_Detect_Min for the minimum time T_Capture_Detect_Min, so that a capture, i.e., successful stimulation of the muscle is detected. Here, the swallowing stimulation program terminates. The same or another program for swallowing may be triggered by selecting a food type displayed on the touch display screen 57 of operating unit 50.

FURTHER EXEMPLARY EMBODIMENTS

In general the following sequence is conceivable:
1. The patient ingests food.
2. The patient selects the corresponding food on his patient device, operating unit 50.
3. Swallowing stimulator 40 is programmed accordingly. The programming parameters are described above.
4. The patient ingests food, the stimulator 40 stimulates a corresponding act of swallowing.
5. If the same food is consumed again, renewed operation of the patient device, operating unit 50, is not necessary.
6. If another food is ingested, the procedure is repeated starting with step 2.

Exemplary Embodiment 1

The Patient Drinks Hot Tea

1. The food to be ingested is liquid.
2. The food to be ingested is (very) hot.

Exemplary embodiment 1 yields the following conclusions:
Because the food is liquid, it need not be chewed.
If the liquid is ingested while very hot, it is cooled because of either the simultaneous intake of air (sipping) or because of the subsequent intake of air (drinking).
This food will not form a food bolus in swallowing but instead, it flows down the esophagus as liquid.
The resulting changes in pressure in the mouth (e.g., a sudden increase in pressure when sipping) and the time for ingestion including cooling (typically 1-5 seconds in sipping, typically 2-5 seconds in the subsequent intake of air) are taken into account by the stimulator system 35. Because the food is liquid, the pressure with which the tongue shapes the food bolus (not shapeable here) is not as high as it is with solid food. The trigger point for stimulation of the swallowing act is programmed so that stimulation of the esophagus typically occurs 1-5 seconds after the start of ingestion of food.

Exemplary Embodiment 2

The Patient Eats a Carrot

1. The food to be ingested is solid and relatively brittle.

Exemplary embodiment 2 yields the following conclusions:
The food must be chewed, here typically 10-20 times.
The chewed food is shaped by the tongue into a contact food bolus. The chewing operation will thus cause 10-20 pressure peaks on the palate. The stimulator 40 is programmed so that it counts the pressure peaks. Once the minimum number of chewing operations has been reached, the stimulation is "activated," i.e., the shaping of the food bolus with the tongue and the shifting of the food bolus with the tongue in the direction of the throat trigger the act of swallowing by stimulation approximately 0.1-2 seconds later after detection of the operation.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A swallowing stimulation system comprising:
    an implantable sensor unit configured to
        detect pressure against a palate of a patient to detect a shaping of a food bolus and generate a detected pressure,
        and
        detect a muscle activity associated with a swallow via an electromyography recording or EMG recording;
    an operating unit comprising a plurality of operating elements, each configured to receive a corresponding patient input, wherein the operating elements are assigned to one or more physical properties of a food, wherein said one or more physical properties comprise a consistency of a particular food; and,
    a swallowing stimulator, configured to
        trigger an act of swallowing in the patient as a function of
            the patient input associated with said operating elements of said operating unit
            and
            the detected pressure
            and
            the detected muscle activity
        based on a set of stimulation parameters that correspond to
            said patient input
            and
            said consistency of said particular food.

2. The swallowing stimulation system according to claim 1, wherein the set of stimulation parameters comprises a plurality of sets of stimulation parameters that are stored in the operating unit and are assigned to respective operating elements, and wherein the operating unit is configured to transmit the set of stimulation parameters to the swallowing stimulator or the sensor unit or both after said operating unit receives said patient input.

3. The swallowing stimulation system according claim 1, wherein the operating unit comprises a graphic display configured to display a plurality of icons that correspond to a respective plurality of consistencies of foods.

4. The swallowing stimulation system according to claim 3, wherein the display comprises a touch screen, and a section of the touch screen is allocated to an icon shown on the display wherein said icon forms a particular one of said plurality of operating elements, and wherein said operating unit is configured to receive said patient input when said icon is activated by said patient.

5. The swallowing stimulation system according to claim 4, wherein the operating unit is configured to accept a double-click and ignore a single-click to avoid inadvertent operation of said swallowing stimulator.

6. The swallowing stimulation system according to claim 4, wherein said stimulation parameters comprise
 a minimum pressure at which to start a minimum time window for pressure to be considered a chew;
 a minimum number of chews to detect before said trigger said act of swallowing is performed;
 a maximum time between two chews;
 a time of stimulation delay between detection of said minimum number of chews and said trigger of said act of swallowing;
 a pulse type of voltage or current;
 a stimulation pulse length;
 a number of stimulation pulses to be delivered at said trigger of said act of swallowing;
 a maximum time after a pulse delivery until a capture is detected by said implantable sensor unit;
 a minimum time that said EMG recording is above a threshold to count said trigger as a successful stimulation;
 a time after said pulse delivery to wait for said capture;
 a backup pulse flag that determines if a backup pulse is delivered if said successful stimulation does not occur.

7. The swallowing stimulation system according to claim 6, wherein said stimulation parameters further comprise
 a morphology flag that determines if pressure velocity is utilized;
 a minimum velocity of pressure rise;
 a minimum velocity of pressure drop.

8. The swallowing stimulation system according to claim 6, wherein said stimulation stimulator is configured to trigger a backup pulse if said EMG recording does not indicate a successful stimulation of a first stimulation pulse initiated by said swallowing stimulator.

* * * * *